US00PP21773P2

(12) United States Plant Patent
Korlipara

(10) Patent No.: US PP21,773 P2
(45) Date of Patent: Mar. 8, 2011

(54) *ECHINACEA* PLANT NAMED 'TANGERINE DREAM'

(50) Latin Name: ***Echinacea* spp.**
Varietal Denomination: Tangerine Dream

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/653,635

(22) Filed: Dec. 14, 2009

(51) Int. Cl.
*A01H 5/00* (2006.01)

(52) U.S. Cl. ..... Plt./428

(58) Field of Classification Search ..... Plt./428
See application file for complete search history.

(56) References Cited

U.S. PATENT DOCUMENTS

PP18,839 P2 * 5/2008 Korlipara ..... Plt./428

* cited by examiner

*Primary Examiner*—Wendy Haas
(74) *Attorney, Agent, or Firm*—Klarquist Sparkman, LLP

(57) ABSTRACT

A new and distinct *Echinacea* plant named 'Tangerine Dream' characterized by medium, bright orange flowers with broad ray florets, well-branched flower stalks, a low habit, and excellent vigor.

1 Drawing Sheet

Botanical denomination: *Echinacea* spp.
Variety designation: 'Tangerine Dream'.

BACKGROUND OF THE INVENTION

The present invention relates to a new and distinct cultivar of *Echinacea* and given the cultivar name 'Tangerine Dream'. *Echinacea* is in the family Asteraceae. This new cultivar originated as a fourth generation seedling from a planned breeding program using the unpatented parents *Echinacea paradoxa* and *Echinacea purpurea* 'Ruby Giant' for the initial cross. The exact parents of this selection are unnamed proprietary, unreleased plants.

Compared to *Echinacea* 'Ruby Giant', an unpatented plant and the original seed parent in the breeding line, the new variety has orange rather than red purple flowers.

Compared to *Echinacea paradoxa*, an unpatented plant and the original pollen parent in the breeding line, the new variety is shorter, orange rather than yellow, with broader ray florets, and with ray florets slightly rather than strongly reflexed.

Compared to *Echinacea* 'Tiki Torch', U.S. Plant Pat. No. 18,839, the new variety is shorter and more branched.

This new *Echinacea* cultivar is distinguished by:

1. medium, bright orange flowers with broad ray florets,
2. well-branched flower stalks,
3. low habit, and
4. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows nine-month-old plants of *Echinacea* 'Tangerine Dream' growing in the ground in the trial field in summer in Canby, Oreg.

FIG. 2 shows a close up of the flowers of the same plants.

DETAILED PLANT DESCRIPTION

The following is a detailed description of the new *Echinacea* cultivar based on observations of a 9-month-old specimen growing in the ground in the field in full sun under typical outdoor conditions in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, 1999 edition.

Plant:

*Type.*—Herbaceous perennial.
*Hardiness.*—USDA Zones 4 to 9.
*Size.*—60 cm wide and 60 cm tall to top of flowers.
*Form.*—Basal clump.
*Vigor.*—Excellent.
*Roots.*—Fibrous, with many downward growing and few laterals, ivory in color, Yellow White 158D, roots develop easily from cuttings from the crown.

Stem (flowering):

*Type.*—Ascending.
*Size.*—Branching to 50 cm tall to a terminal flower and 8 mm wide at base.
*Internode length.*—2.5 cm to 7 cm.
*Surface texture.*—Strigose.
*Color.*—Yellow Green 146C mottled with Yellow Green 144B and tinted with a slight pink tone in high light (Greyed Red 182B).

Leaf (basal):

*Type.*—Simple.
*Shape.*—Lanceolate.
*Arrangement.*—Basal.

*Blade size.*—Grows to 11.5 cm long and 4 cm wide.
*Margins.*—Shallowly broadly serrate.
*Apex.*—Acute.
*Base.*—Attenuate, continuing down petiole, clasping.
*Surface texture.*—Strigose on both sides.
*Venation.*—Pinnate.
*Color.*—Topside, Yellow Green 147A with the vein Yellow Green 147D and bottom side closest to Yellow Green 147B with the vein Yellow Green 147D.
*Petiole description.*—Grows to 14 cm long and 2.5 mm wide, strigose, Yellow Green 146B.

Leaf (stem):
*Type.*—Simple.
*Shape.*—Lanceolate.
*Arrangement.*—Alternate.
*Blade size.*—Grows to 6.5 cm long and 4 cm wide.
*Margins.*—Slightly undulate and entire on stem.
*Apex.*—Acute.
*Base.*—Attenuate, continuing down petiole, clasping.
*Surface texture.*—Strigose on both sides.
*Venation.*—Pinnate.
*Color.*—Topside, Yellow Green 147A with the vein Yellow Green 146D and bottom side closest to Yellow Green 147B with the vein Yellow Green 146D.
*Petiole description.*—Grows to 6 cm long on lower leaves to sessile on upper leaves and 4 mm wide, strigose, Yellow Green 147D.

Inflorescence:
*Type.*—Composite on terminal stalked heads.
*Number of flowering stems per plant in summer.*—3 to 5.
*Flowering stem.*—Grows to 50 cm tall from the base of the plant to the terminal flower and can grow to 17 cm long from the top leaf to the base of a flower head; branched, about 14 flowers per stem; diameter growing to 8 mm wide near the flower head; strigose, Yellow Green 146C mottled with Yellow Green 144B and tinted with a slight pink tone in high light (Greyed Red 182B).
*Size.*—Grows to 10.5 cm wide and 5.5 cm deep as disc enlarges.
*Form.*—Ray petals cup downward slightly, mature disc is conic.
*Immature inflorescence.*—4 cm wide and 2.5 cm deep, ray florets held at a 45 degree angle and rolled up so only the back color shows, Greyed Red 182B except on inside tip where Greyed Yellow 162B, disc is Brown 200A with the center Yellow Green 144A.
*Ray florets.*—Without pistil or stamen, 19 to 21 in number, oblanceolate with the tip two toothed (each acute), entire margins, base attenuate, grows to 6 cm long and 16 mm wide, glabrous on both sides; topside color of young mature ray florets between Greyed Orange 169B and Orange 28A on the top half darkening to Greyed Orange 169A on the bottom half; oldest florets lighten Greyed Orange 163A on top ⅔ and blending to Greyed Red 180A at the base, bottom side closest to Greyed Red 182C.
*Disc.*—Slightly convex becoming conic, becoming 38 mm long and 40 mm wide with maturity, overall color Brown 200B.
*Disc florets.*—About 380 in number, each 9 mm long and 2.5 mm wide, each with one persistent, very stiff bract (12 mm long and Greyed Purple 187A on tip, Yellow Green 144A to 144D on bottom half); corolla 6.5 mm long and 1.5 mm wide, 5 lobed, glabrous, Yellow Green 145C to 145B with lobes tips Greyed Purple 187B; pistil 10 mm long, ovary 2 mm long, White 155A, style 6 mm long Yellow Green 145D, with an extruding, 2-branched stigma spreading 3.5 mm wide, Greyed Purple 187B; stamen 4 in number, 5 mm long, anthers 3.5 mm long and Black 202A, filaments 1.5 mm long, Yellow White 158D, pollen Yellow Orange 17A.
*Phyllaries.*—In 4 leafy series, area 3.7 cm wide and 6 mm deep, lobes lanceolate in shape, reflexed, grow to 15 mm long and 3 mm wide, Yellow Green 147B, margins strigose, tip acute.
*Receptacle.*—Grows to 11 mm wide and 20 mm deep, White 155D.
*Bloom period.*—July through October in Canby, Oreg.
*Fragrance.*—Lovely, floral.
*Lastingness.*—Each inflorescence lasts about two weeks in Canby, Oreg.
*Seeds.*—Average number of 7 seeds/head, each 5 mm long and 2.5 mm wide, oval, Brown 200C.
*Fertility.*—Good.

Disease and pests: *Echinacea* are susceptible to leaf miners, powdery mildew, bacterial spots, and gray mold. None of these have been observed on plants grown under commercial conditions in Canby, Oreg. No resistance is known.

I claim:

1. A new and distinct *Echinacea* plant as herein illustrated and described.

* * * * *

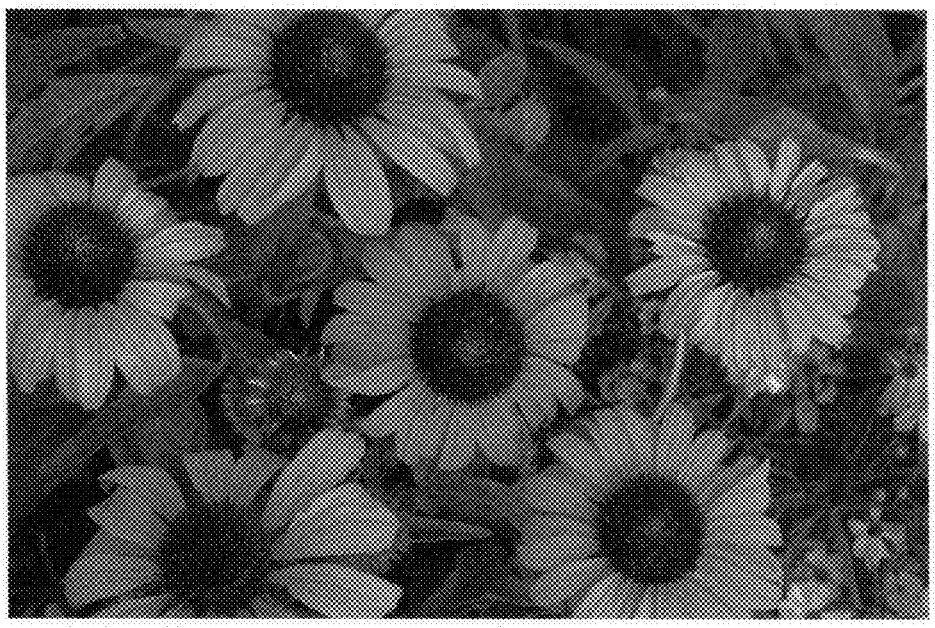

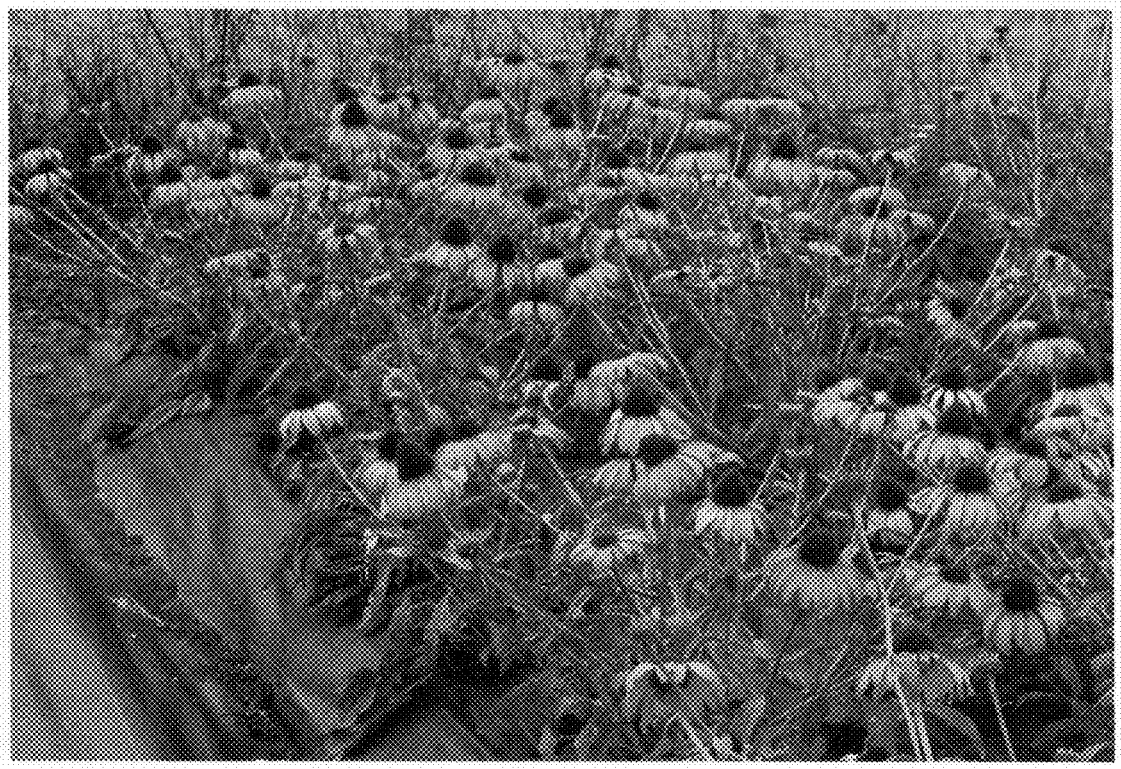
Figure 1 above, Figure 2 below.